(12) United States Patent
Brockhoff et al.

(10) Patent No.: US 6,827,862 B1
(45) Date of Patent: Dec. 7, 2004

(54) METHOD AND DEVICE FOR REMOVING GAS FROM GAS CONTAINING BLOOD

(76) Inventors: Alexander Brockhoff, Gebhardstorkel 10, FL-9494 Schaan (LI); Hans Plechinger, Cherry Creek Ranch, SS 3 Site 15-130 Cranbrook B.C. (CA)

(*) Notice: Subject to any disclaimer, the term of this patent is extended or adjusted under 35 U.S.C. 154(b) by 0 days.

(21) Appl. No.: 08/938,173

(22) Filed: Sep. 26, 1997

(30) Foreign Application Priority Data

May 9, 1997 (DE) .......................... 197 19 555

(51) Int. Cl.[7] .......................... B01D 21/26; B01D 19/00
(52) U.S. Cl. .......................... 210/787; 55/459.1; 96/155; 96/204; 210/188; 210/512.1; 210/782; 210/788
(58) Field of Search .......................... 210/188, 512.1, 210/782, 787, 788; 55/459.1, 459.2, 459.3, 459.5; 96/155, 204; 209/715, 725

(56) References Cited

U.S. PATENT DOCUMENTS

| | | |
|---|---|---|
| 2,876,860 A | 3/1959 | Clark et al. |
| 3,715,863 A | 2/1973 | Zanoni |
| 3,753,336 A | 8/1973 | Drew et al. .................. 55/242 |
| 3,771,290 A | 11/1973 | Stethem .................. 210/304 |
| 3,785,380 A | 1/1974 | Brumfield .................. 128/276 |
| 3,807,401 A | 4/1974 | Riggle et al. |
| 3,812,655 A | 5/1974 | Bennett |
| 3,833,013 A | 9/1974 | Leonard |
| 3,912,468 A | 10/1975 | Tsuchiya et al. |
| 3,955,573 A | 5/1976 | Hansen et al. |
| 3,965,896 A | 6/1976 | Swank |
| 3,994,689 A | 11/1976 | DeWall |
| 3,996,027 A | 12/1976 | Schnell et al. |
| 4,053,291 A | 10/1977 | Sims |
| 4,054,522 A | 10/1977 | Pinkerton .................. 210/188 |
| 4,061,031 A | 12/1977 | Grimsrud .................. 210/188 |
| 4,093,428 A | 6/1978 | Swogger |

(List continued on next page.)

FOREIGN PATENT DOCUMENTS

| | | |
|---|---|---|
| DE | 2261127 | 6/1973 |
| DE | 26 11 383 A | 9/1977 |
| DE | 2621051 | 12/1977 |
| DE | 3011681 | 10/1980 |
| DE | 3222345 | 1/1983 |
| DE | 3641644 | 10/1987 |
| DE | 3624363 | 1/1988 |
| DE | 3448173 | 2/1989 |
| DE | 43 26 886 A | 2/1995 |
| DE | 4329385 | 3/1995 |
| DE | 4326886 | 8/1995 |
| DE | 29500879 | 3/1996 |
| DE | 19545404 | 6/1997 |
| EP | 318 993 A | 6/1989 |
| EP | 778031 | 11/1997 |
| GB | 1 352 166 | 5/1974 |
| GB | 1526509 | 9/1978 |
| GB | 2063108 | * 6/1981 |
| JP | 46-4444 | 11/1971 |
| JP | 49-15341 | 4/1974 |
| WO | 92020380 | 11/1992 |

*Primary Examiner*—John Kim
(74) *Attorney, Agent, or Firm*—Beck & Tysver P.L.L.C.

(57) ABSTRACT

A method and device for removing gas from gas containing blood. A non-rotating cyclone eddy chamber has the blood circulating therein and centrifugal force separates the blood radially outward and the gas radially inward. The cyclone inlet comprises a blood inlet channel that extends in a helical circular form developed to narrow in funnel like manner in the direction of flow toward the cyclone eddy chamber to accelerate the blood flow entering that chamber tangentially. A gas outlet is arranged in the radially inner center of the cyclone eddy chamber path while the blood outlet is coaxial and outward of the gas outlet.

3 Claims, 1 Drawing Sheet

U.S. PATENT DOCUMENTS

| | | | | |
|---|---|---|---|---|
| 4,102,655 | A | 7/1978 | Jeffery et al. | 210/188 |
| 4,247,309 | A | 1/1981 | Buddenhagen | |
| 4,282,016 | A | 8/1981 | Tauber et al. | 210/512.1 |
| 4,316,271 | A | 2/1982 | Evert | 73/644 |
| 4,344,777 | A | 8/1982 | Siposs | 210/436 |
| 4,345,919 | A | 8/1982 | Wilkinson et al. | 210/436 |
| 4,360,428 | A | 11/1982 | Comparetto et al. | 210/188 |
| 4,368,118 | A | 1/1983 | Siposs | 210/436 |
| 4,388,922 | A | 6/1983 | Telang | 604/319 |
| 4,394,138 | A | 7/1983 | Schilling | 210/512.1 |
| 4,433,971 | A | 2/1984 | Lindsay et al. | 604/122 |
| 4,474,184 | A | 10/1984 | Harui | 72/644 |
| 4,475,932 | A | 10/1984 | Hull et al. | 210/188 |
| 4,547,186 | A | 10/1985 | Bartlett | 604/4 |
| 4,555,253 | A | 11/1985 | Hull et al. | 210/188 |
| 4,585,465 | A | 4/1986 | Suzuki et al. | 210/788 |
| 4,690,762 | A | 9/1987 | Katsura | 210/436 |
| 4,710,299 | A | 12/1987 | Prendergast | |
| 4,749,387 | A | 6/1988 | Lotz | 55/269 |
| 4,806,135 | A | 2/1989 | Siposs | 210/456 |
| 4,860,591 | A | 8/1989 | Garland | 73/861.04 |
| 4,874,359 | A | 10/1989 | White et al. | 604/4 |
| 4,900,308 | A | 2/1990 | Verkaart | 604/406 |
| 4,940,473 | A | 7/1990 | Benham | 55/417 |
| 4,966,703 | A * | 10/1990 | Kalnins et al. | 210/512.1 |
| 5,061,236 | A | 10/1991 | Sutherland et al. | 604/4 |
| 5,152,964 | A | 10/1992 | Leonard | 422/48 |
| 5,188,604 | A | 2/1993 | Orth | 604/153 |
| 5,228,889 | A | 7/1993 | Cortial et al. | |
| 5,411,472 | A | 5/1995 | Steg, Jr. et al. | 604/4 |
| 5,429,595 | A | 7/1995 | Wright, Jr. et al. | 604/9 |
| 5,451,321 | A | 9/1995 | Matkovich | 210/641 |
| 5,486,162 | A | 1/1996 | Brumbach | 604/22 |
| 5,503,801 | A | 4/1996 | Brugger | 422/44 |
| 5,531,119 | A | 7/1996 | Meyers | 73/661 |
| 5,537,335 | A | 7/1996 | Antaki et al. | 364/510 |
| 5,582,633 | A | 12/1996 | Jiang et al. | 96/102 |
| 5,591,251 | A | 1/1997 | Brugger | 604/4 |
| 5,632,894 | A | 5/1997 | White et al. | 210/436 |
| 5,674,199 | A | 10/1997 | Brugger | 604/122 |
| 5,707,431 | A | 1/1998 | Verkaart et al. | 210/430 |
| 5,755,965 | A * | 5/1998 | Reiber | 210/512.1 |
| 5,824,212 | A * | 10/1998 | Brockhoff | 210/194 |

* cited by examiner

US 6,827,862 B1

METHOD AND DEVICE FOR REMOVING GAS FROM GAS CONTAINING BLOOD

BACKGROUND OF THE INVENTION

The present invention relates to a method and device for removing gas from gas containing blood by operation of a centrifuging device.

This type of device is disclosed in British A-2 063 108. Further devices for separating gas from gas containing blood are described in U.S. Pat. Nos. 3,785,380, 4,368,118, 4,388,922 and 5,451,321, as well as in German DE-C-36 24 363 and 36 41 644 and DE-A-43 29 385.

Blood given to a patient should not contain any air or other gas, even in the form of micro-small bubbles of gas. The blood is fed to the patient by a pressure pump. Although that is the preferred field of use of the invention, it does not exclude the invention also being used to remove air from blood which is drawn from a patient at the site of a wound, since it frequently cannot be avoided that air is also drawn into the bloodstream at the site of the wound. The air must be removed from the blood as rapidly as possible and as close as possible to the wound since it can otherwise damage the blood. Other possible fields of use of the invention are the removal of gas from gas-containing blood which is transported from one instrument to another or to a container.

SUMMARY OF THE INVENTION

The object of the invention is to improve the efficiency of the gas removal and, in particular, to provide a method and a device with which even micro-small bubbles of gas can be removed from gas containing blood, even if the gas containing blood is being conveyed in a large volume per unit of time.

The invention concerns a method and device for removing gas from gas containing blood. A non-rotating cyclone eddy chamber has the blood circulating therein and centrifugal force separates the blood radially outward and the gas radially inward. The cyclone inlet comprises a blood inlet channel that extends in a helical circular form developed to narrow in funnel like manner in the direction of flow toward the cyclone eddy chamber to accelerate the blood flow entering that chamber tangentially. A gas outlet is arranged in the radially inner center of the cyclone eddy chamber path while the blood outlet is coaxial and outward of the gas outlet.

Other objects, features and advantages of the present invention will become apparent from the following description of the invention which refers to the accompanying drawing.

DETAILED DESCRIPTION OF THE INVENTION

Figure 1:
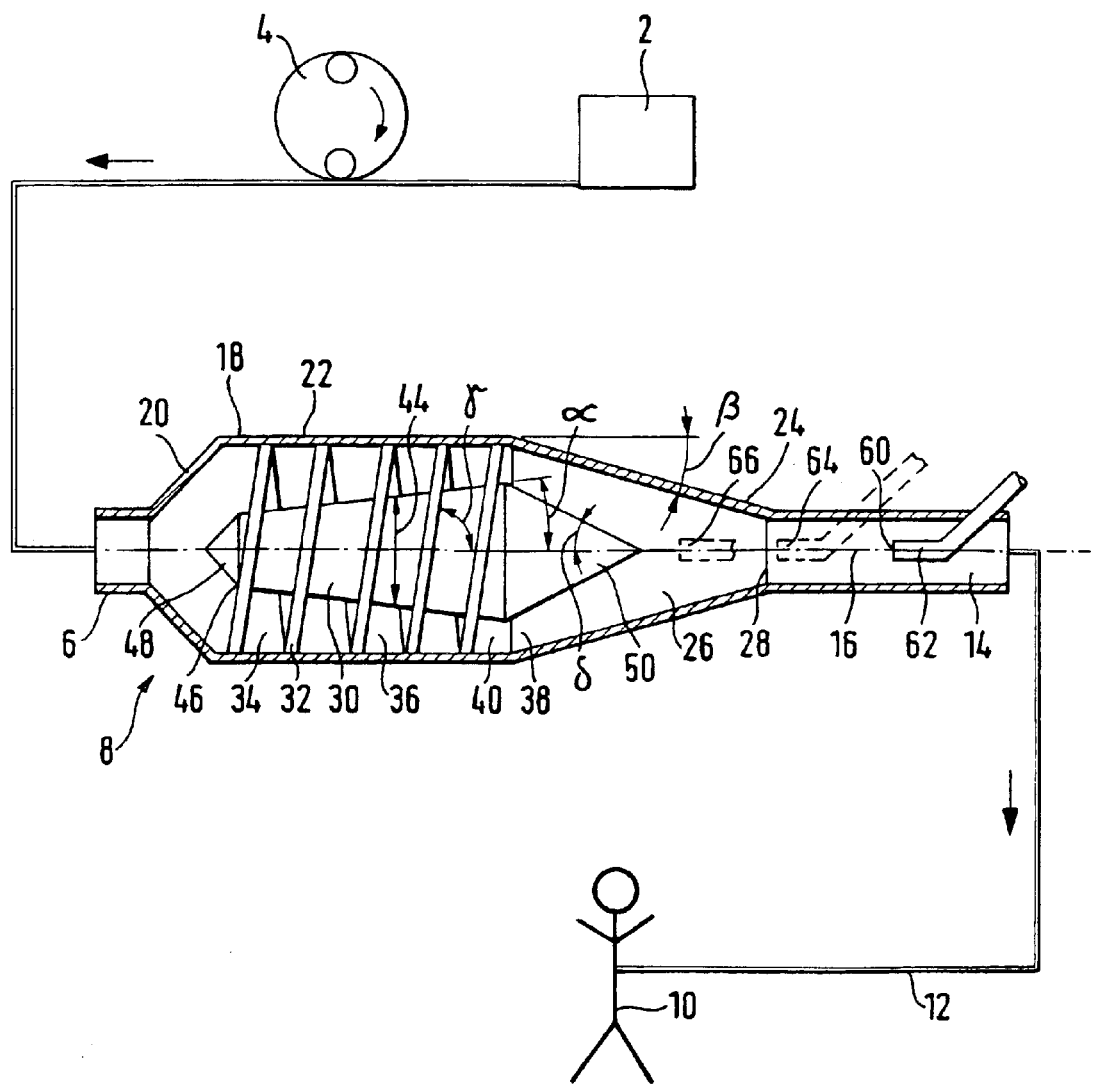
FIG. 1 diagrammatically shows, in part in axial section, a device in accordance with the invention for removing gas from gas containing blood.

FIG. 1 shows a source of blood 2, which may be a device known in medicine, for instance, a blood oxygenator, a heart-lung machine, a blood filter, a reservoir, a cardioplegia system, a plasmaphoresis system, a dialysis system, or some other blood transfusion system. The blood source is connected by a pressure pump 4 to an input 6 of a cyclone, eddy current device 8 and conducts blood through the device 8 to a patient 10 or an instrument. This instrument or the patient 10 is connected via a hose 12 to a cyclone outlet channel 14 of the cyclone eddy current device 8.

The cyclone eddy current device 8 contains, arranged coaxially one behind the other along a linear center axis 16, a housing 18 of circular cross section with its inlet 6 at one axial end and its outlet channel 14 on the other axial end. The housing inlet 6 has, arranged axially one behind the other, an inlet section 20 which widens in funnel like manner in the direction of flow, followed by a cylindrical channel section 22 and then by a cyclone eddy chamber section 24 which narrows down in a funnel like manner in the direction of flow and forms the circumferential wall of a cyclone eddy chamber 26 which narrows down in a funnel like manner in the same way. The gas containing mixture of blood rotates with constant direction of rotation within the cyclone eddy chamber 26 from the axial inlet starting point of the chamber to the axial outlet end of the chamber. Here, the mixture of blood and gas is separated by centrifugal force into a radially outer blood phase (blood portion) and a radially inner gas phase (gas portion). The downstream end 28 of the cyclone eddy chamber 26 is connected to the upstream starting point of the outlet channel 14 and forms a cyclone outlet for the blood phase.

Within the channel section 22 of the housing 18 and coaxial to the center axis 16, there is an insert body 30 which has at least one wider diameter helical rib 32. Between adjacent coils of the rib and the body 30, at least one helical groove 34 is formed. Together, the surrounding wall of the housing, which the rib 32 engages, the groove or grooves 34 define a helical blood inlet channel 36. The blood inlet channel 36 extends from a point downstream of the inlet 6 up to the upstream starting point 38 of the cyclone eddy chamber 26 to there defines a substantially tangential cyclone inlet 40 from which the gas containing blood flows substantially tangentially into the cyclone eddy chamber 26. The blood then flows in a cyclone eddy current up to the end 28 of the chamber, and after passing that end and further rotating, it passes into the outlet channel 14. The cyclone eddy chamber 26 can be developed so as to narrow in funnel shape over its entire length, as shown in FIG. 1, or it may have a circular cylindrical shape, at least at its upstream initial section. The funnel like narrowing shape of the cyclone eddy chamber 26 is to maintain the cyclone centrifugal energy over the entire axial length of the cyclone eddy chamber 26.

The diameter 44 of the insert body 30 at the base of the grooves 34 is smallest at the upstream starting point 46 of a groove and increases downstream in the direction of flow up to the cyclone inlet 40, i.e., the diameter of the groove decreases and its volume decreases. The channel section 22 of the housing 18 which limits the grooves 34 at the outside circumference can have a shape other than circular cylindrical. In any event, it is so shaped that the helical blood inlet 36 defined by the ribs 32, the grooves 34 and the channel section 22 has, at least over a part of its length but preferably over its entire length, a flow cross section which becomes continuously smaller in funnel like manner in the direction of flow so that the gas containing blood is accelerated downstream in it and flows with the greatest possible speed into the cyclone eddy chamber 26.

The ribs 32 can rest against the channel section 22 or be a small distance in from it. On its upstream starting point, the insert body 30 preferably has a conical tip 48 directed opposite the flow of blood. At its downstream end, the body 30 has a conical tip 50 directed narrower in the direction of flow. Instead of such conical tips 48 and 50, the insert body 90 may also have rounded or flat end surfaces.

The angles shown in the drawing have preferably the following size ranges: angle α between the center line 16 and a generatrix of the insert body 30 on the bottom of the grooves 34: 0° to 30°; angle β between the channel section 22 of the housing 18 and the cyclone eddy chamber section 24 of the housing 18: 0° to 45°; the angle γ between the center line 16 and an end of the rib 32 transverse to the center line 16: 45° to 80°, and the angle δ of the downstream conical tip 50 between the center line 16 and the generatrix of this conical tip 50: 90° to 150°. If the angle α between the center line 16 and the lengthwise line on the bottom of the grooves 34 is 0° or only a few degrees, then the lengthwise line of the channel section 22 should pass in the direction of flow of the blood obliquely to the center line 16 so that the grooves 34 of the blood inlet channel 36 have a cross sectional size which becomes narrower in wedge like manner in the direction of flow of the blood. As another possibility for developing the grooves 34 and thus also the blood inlet channel 36 in a manner which narrows down in funnel like manner in the direction of flow, the distance between the ribs 32 continuously decreases in the direction of flow. In these ways, the height and/or width of the grooves 34 can be changed to gradually decrease the volume of the groove downstream.

The gas containing blood which enters tangentially into the cyclone eddy chamber 26 at the cyclone inlet 40 flows in the form of a cyclone eddy current, through the cyclone eddy chamber 26 to its outlet end 28. This produces centrifugal forces which force the blood phase or blood portion of the gas containing blood into the radially outer cyclone eddy current region. As the blood phase is heavier than the gas contained in the blood, this forces the gas or the gas phase into the radially inner cyclone eddy current region. The cyclone eddy current travels into the outlet channel 14.

Within the radially inner center of this cyclone eddy current, a gas outlet opening 16 is arranged coaxial to the center line and facing in the direction opposite the axial flow of the blood phase and the gas phase, so that the gas phase can flow only from a small cross-sectional region in and around the center line 16 into the gas outlet opening 60. The gas outlet opening 60 can, for instance, be arranged up to 10 cm downstream of the downstream end 28 of the cyclone eddy chamber 26, and this is shown by a gas line 62 arranged coaxially in the outlet channel 14 or at the downstream end 28, as shown in dashed line at 64, or even upstream of the end 28, as shown diagrammatically at 66. In all cases, the gas outlet opening 60 is located coaxially on the center line 16 and is directed opposite the axial direction of flow of the gas phase and the blood phase.

In the embodiment shown, the inlet 6, the eddy chamber 26, the outlet channel 14, the gas outlet opening 60, and at least the initial section of the gas line 62 within which the gas outlet opening 60 is formed are all arranged coaxial to the linear center line 16.

In a modified embodiment of the invention, the direction of the inlet 6 can lie in a region which is between an axial direction and a tangential direction to the center line 16, the tangential direction pointing in the same circumferential direction as the grooves 34, so that the flow of blood is not reversed when entering the chamber 26. Furthermore, the direction of the blood outlet channel 14 and/or the direction of the gas outlet opening 60 and of its gas line 62, or at least of the initial section of this gas line 62, can lie in a region between the axial forward direction in accordance with FIG. 1 and the tangential direction of movement of the cyclone eddy current.

Although the present invention has been described in relation to a particular embodiment thereof, many other variations and modifications and other uses will become apparent to those skilled in the art. It is preferred, therefore, that the present invention be limited not by the specific disclosure herein, but only by the appended claims.

What is claimed is:

1. A device for extracting gas bubbles from blood comprising:
    a housing having an input channel and an outlet channel; said input channel and said outlet channel being concentric along a housing axis;
    a chamber section coupled to said input channel and located after said input channel, said chamber section having a chamber interior wall;
    an eddy chamber coupled to said chamber section and located after said chamber section;
    an outlet channel coupled to said eddy chamber and located after said eddy chamber;
    an insert body located in said chamber section and extending into said eddy chamber;
    at least one rib extending between said insert body and said chamber section interior wall, forming a helical groove in said chamber section and not extending into said eddy chamber;
    said helical groove having constant cross sectional area but variable pitch along its length;
    a gas outlet located along said axis in said eddy chamber; whereby blood containing gas bubbles entering said input channel are directed into said chamber section where said helical groove accelerates said blood and causes it to enter said eddy chamber.

2. A device for extracting gas bubbles from blood comprising:
    a housing having an input channel and an outlet channel; said input channel and said outlet channel being concentric along a housing axis;
    a chamber section coupled to said input channel and located after said input channel, said chamber section having a chamber interior wall
    an eddy chamber coupled to said chamber section and located after said chamber section;
    an outlet channel coupled to said eddy chamber and located after said eddy chamber;
    an insert body located in said chamber section and extending into said eddy chamber;
    at least one rib extending between said insert body and said chamber section interior wall, forming a helical groove in said chamber section and not extending into said eddy chamber;
    said helical groove having variable cross sectional area but constant pitch along its length;
    a gas outlet located along said axis in said outlet channel; whereby blood containing gas bubbles entering said input channel are directed into said chamber section where said helical groove accelerates said blood and causes it to enter said eddy chamber.

3. A method of removing gas bubbles from blood comprising the steps of:
    introducing blood into a helical groove where it is accelerated both axially and radially forming an accelerated blood flow;
    introducing said accelerated blood flow into an eddy chamber along a tangent, where said blood is allowed to continue to turn while decelerating;
    extracting a portion of said blood flow from a location near the central axis of flow.

* * * * *